US011666258B2

(12) United States Patent
Shojaeizadeh et al.

(10) Patent No.: US 11,666,258 B2
(45) Date of Patent: Jun. 6, 2023

(54) EYE-TRACKING SYSTEM FOR DETECTION OF COGNITIVE LOAD

(71) Applicant: WORCESTER POLYTECHNIC INSTITUTE, Worcester, MA (US)

(72) Inventors: Mina Shojaeizadeh, Worcester, MA (US); Soussan Djamasbi, Natick, MA (US); Randy C. Paffenroth, Worcester, MA (US); Andrew C. Trapp, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 880 days.

(21) Appl. No.: 16/523,147

(22) Filed: Jul. 26, 2019

(65) Prior Publication Data

US 2020/0029806 A1   Jan. 30, 2020

Related U.S. Application Data

(60) Provisional application No. 62/711,057, filed on Jul. 27, 2018.

(51) Int. Cl.
| A61B 5/16 | (2006.01) |
| A61B 3/113 | (2006.01) |
| G06F 3/01 | (2006.01) |
| G06F 9/54 | (2006.01) |
| G06T 7/20 | (2017.01) |
| G06N 20/00 | (2019.01) |
| G06F 18/214 | (2023.01) |
| G06V 40/19 | (2022.01) |

(52) U.S. Cl.
CPC .............. *A61B 5/163* (2017.08); *A61B 3/113* (2013.01); *G06F 3/013* (2013.01); *G06F 3/017* (2013.01); *G06F 9/542* (2013.01); *G06F 18/214* (2023.01); *G06N 20/00* (2019.01); *G06T 7/20* (2013.01); *G06V 40/19* (2022.01)

(58) Field of Classification Search
CPC ..... A61B 3/113; A61B 5/163; A61B 2503/24; G06F 3/013; G06F 3/017; G06F 9/542; G06K 9/6256; G06N 20/00; G06N 20/20; G06T 7/20; G06V 40/19
See application file for complete search history.

(56) References Cited

U.S. PATENT DOCUMENTS

| 2009/0086165 | A1* | 4/2009 | Beymer | A61B 3/113 351/210 |
| 2009/0232357 | A1* | 9/2009 | Angell | G06V 20/52 382/103 |

(Continued)

*Primary Examiner* — Pei Yong Weng
(74) *Attorney, Agent, or Firm* — Duquette Law Group

(57) ABSTRACT

A visual tracking system, comprises an eye-tracking device and a cognitive load detection device disposed in electrical communication with the eye-tracking device, the cognitive load detection device comprising a controller having a memory and a processor. The controller is configured to receive eye-movement data from the eye-tracking device, the eye-movement data comprising pupil dilation event data and at least one of saccade event data and fixation event data, apply a classification function to the eye-movement data to detect a cognitive load associated with the eye-movement data and corresponding to a visual location of a field of view of the user, and output a notification regarding the cognitive load associated with the eye-movement data.

16 Claims, 4 Drawing Sheets

(56) References Cited

U.S. PATENT DOCUMENTS

2010/0217097 A1\* 8/2010 Chen ................... G16H 50/20
600/300
2016/0170584 A1\* 6/2016 Kumar ................. G06F 3/0484
715/810

\* cited by examiner

EYE-TRACKING SYSTEM FOR DETECTION OF COGNITIVE LOAD

RELATED APPLICATIONS

This patent application claims the benefit of U.S. Provisional Application No. 62/711,057, filed on Jul. 27, 2018, entitled, "Automatic Detection of Cognitive Demand via an Eye Tracking Machine Learning System," the contents and teachings of which is hereby incorporated by reference in its entirety.

BACKGROUND

Many complex tasks involve the use of visual displays, such as computer displays. Individuals using these displays are required to make efficient visual searches of their screens to review and/or locate pertinent information. To evaluate an individual's performance as well as a display's usefulness, it is considered desirable to know precisely where and for long an individual looks at the display during critical times. In addition, in assessing the effectiveness of any visual display, it is useful to know not only what features of the display an individual focuses on, but whether cognitive activity occurs.

Eye-tracking provides a metric that can measure what a user read/viewed on the display and can identify cognitive processing associated with the viewing. Conventional eye-tracking devices are configured to record eye-tracking, or gaze, data of a subject that is presented a visual stimulus and to perform fixation identification associated with the eye-tracking data. Fixation identification separates eye-tracking data into fixations and saccades. Fixations identify pauses over regions of interest of the visual display, such as where cognitive processing is believed to occur. Saccades relate to relatively rapid movements of a user's eye between fixations.

SUMMARY

As provided above, conventional eye tracking devices can be utilized to detect items that a user has viewed, such as on a display screen. The resulting eye-tracking data, or gaze data, can be categorized into two main events or categories: fixations which represent focused eye movement, indicative of awareness and attention, and saccades which represent relatively higher velocity movements that occur between fixation events.

By contrast to conventional eye-tracking devices, embodiments of the present innovation relate to an eye-tracking system for detection of cognitive load. Conventionally, mental tasks having a higher demand will require an increased amount of cognitive effort. Further, cognitive effort or load can be reflected in ocular behavior. Therefore, in one arrangement, a cognitive load detection device of the eye tracking system is configured to receive fixation event and saccade event data in combination with pupil dilation event data from an eye-tracking device. The cognitive load detection device can include a classification function which has been trained on a training data set that relates eye-movement data to known task demands or cognitive load. The cognitive load detection device can apply the classification function to the event data to predict a user's cognitive load relative to a given location in a field of view, such as a display. By utilizing combined fixation event and saccade event data with the pupil dilation event data, the cognitive load detection device can predict a user's cognitive load with a relatively high degree of accuracy. Based upon the predicted cognitive load, the cognitive load detection device can output a notification, such as a customized or personalized notification, to the user in order to adjust the user's task demand associated with the field of view. Accordingly, by detecting cognitive load through the analysis of eye-movement data, the eye-tracking system can respond to the user's needs at a personalized level.

Embodiments of the innovation relate to a visual tracking system, comprising an eye-tracking device and a cognitive load detection device disposed in electrical communication with the eye-tracking device, the cognitive load detection device comprising a controller having a memory and a processor. The controller is configured to receive eye-movement data from the eye-tracking device, the eye-movement data comprising pupil dilation event data and at least one of saccade event data and fixation event data, apply a classification function to the eye-movement data to detect a cognitive load associated with the eye-movement data and corresponding to a visual location of a field of view of the user, and output a notification regarding the cognitive load associated with the eye-movement data.

Embodiments of the innovation relate to, in a cognitive load detection device, a method for detecting cognitive load, comprising receiving eye-movement data from an eye-tracking device, the eye-movement data comprising pupil dilation event data and at least one of saccade event data and fixation event data; applying a classification function to the eye-movement data to detect a cognitive load associated with the eye-movement data and corresponding to a visual location of a field of view of the user; and outputting a notification regarding the cognitive load associated with the eye-movement data.

BRIEF DESCRIPTION OF THE DRAWINGS

The foregoing and other objects, features and advantages will be apparent from the following description of particular embodiments of the innovation, as illustrated in the accompanying drawings in which like reference characters refer to the same parts throughout the different views. The drawings are not necessarily to scale, emphasis instead being placed upon illustrating the principles of various embodiments of the innovation.

DETAILED DESCRIPTION

Embodiments of the present innovation relate to an eye-tracking system for detection of cognitive load. Conventionally, mental tasks having a higher demand will require an increased amount of cognitive effort. Further, cognitive effort or load can be reflected in ocular behavior. Therefore, in one arrangement, a cognitive load detection device of the eye tracking system is configured to receive fixation event and saccade event data in combination with pupil dilation event data from an eye-tracking device. The cognitive load detection device can include a classification function which has been trained on a training data set that relates eye-movement data to known task demands or cognitive load. The cognitive load detection device can apply the classification function to the event data to predict a user's cognitive load relative to a given location in a field of view, such as a display. By utilizing combined fixation event and saccade event data with the pupil dilation event data, the cognitive load detection device can predict a user's cognitive load with a relatively high degree of accuracy. Based upon the predicted cognitive load, the cognitive load detection device can output a notification, such as a customized or personalized notification, to the user in order to adjust the user's task demand associated with the field of view. Accordingly, by detecting cognitive load through the analysis of eye-movement data, the eye-tracking system can respond to the user's needs at a personalized level.

Figure 1:
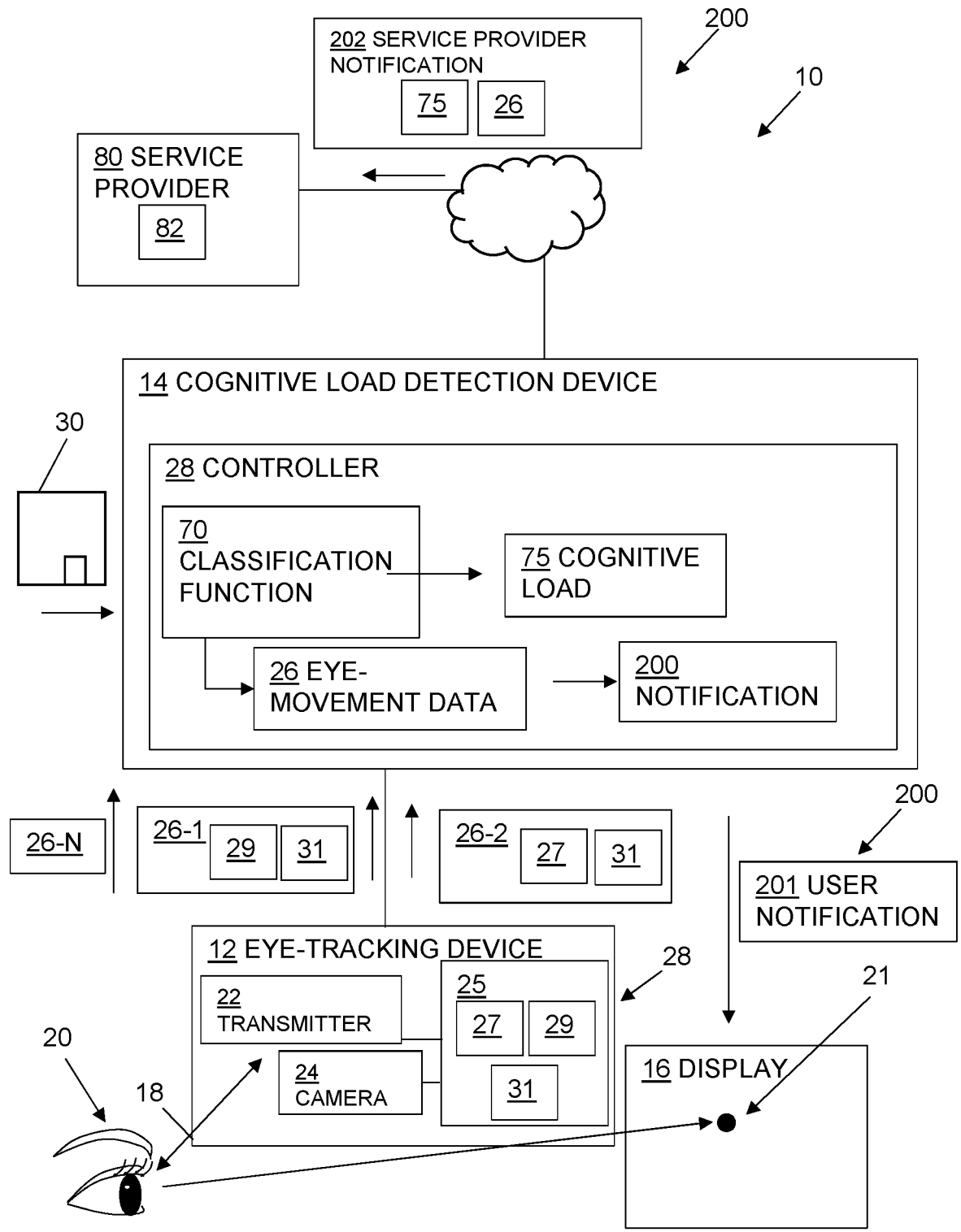
FIG. 1 illustrates a schematic diagram of a visual tracking system, according to one arrangement.

FIG. 1 illustrates a schematic representation of a visual tracking system 10, according to one arrangement. As illustrated, the visual tracking system 10 includes an eye-tracking device 12 disposed in electrical communication with a cognitive load detection device 14.

The eye-tracking device 12 is configured to detect the position of a user's eye relative to a field of view, such as a display 16 or any image received by the user, whether generated electronically or otherwise, based upon the measured position of the user's eye in space. In one arrangement, the eye-tracking device 12 can include an infra-red (IR) transmitter 22 and camera 24 disposed in electrical communication with a controller 25, such as a processor and a memory. For example, the eye-tracking device 12 can be a Tobii TX300 remote eye tracker (Tobii Technology AB, Sweden).

During operation, the transmitter 22 is configured to direct a light 18, such as an infrared (IR) light, against a user's eye 20. The light 18 allows the camera 24 of the eye-tracking device 12 to identify the pupil of the eye and creates a glint on the surface of the eye 20. The position of the glint relative to the eye-tracking device 12 is substantially stationary. As the user's eye and pupil moves to identify and track various items, such as provided on the display 16, the glint acts as a reference point for the camera 24. Accordingly, during operation, the eye-tracking device 12 is configured to identify the user's eye movements relative to the glint.

For example, with reference to FIG. 1, as a user visually focuses on a field of view, such as the display 16, the controller 25 of the eye-tracking device 12 detects user's eye position in three dimensions (x, y, z) of the user's pupil when viewing a location 21 in a field of view, such as a display 16, and projects the user's eye position into two dimensions (x, y in another coordinate system), so that the two-dimensional coordinate represents where the user is looking in a field of view, such as on the display 16. Based upon the detected positioning of the pupil relative to the glint, the eye-tracking device 12 collects a vertical and lateral coordinate (x, y) of the user's visual focus on the location 21 on the display 16, termed a gaze position data element.

For each gaze position data element collected, the controller 25 can also collect an associated time measurement (t). For example, the eye-tracking device 24 can be configured to collect gaze position data elements 28 at a rate between about 10 Hz and 1250 Hz. Assuming the case where the eye-tracking device 12 collects data at a rate of 30 Hz, for each gaze position data element 28 collected, the eye-tracking device 12 associates a corresponding time of $\frac{1}{30}$ second.

Based upon the gaze position data elements 28 received from the eye-tracking device 12, the fixation identification device 14 can identify the position of the user's eyes relative to an image, such as a website, provided by the display 16. For example, the eye-tracking device 12 can identify the gaze position data elements 28 as either fixation event data 27 or saccade event data 29. Fixation event data 27, identify fixations or pauses over informative regions of interest, along with the associated vertical and lateral coordinates (x, y). By contrast, saccade event data 29 identify relatively rapid movements, or saccades, between fixations used to recenter the eye on a new location, along with the vertical and lateral coordinate (x, y).

The controller 25 of the eye-tracking device 12 is also configured to collect pupil dilation event data 31 when collecting gaze position data elements 28. In one arrangement, when collecting either fixation event data 27 or saccade event data 29, the controller 25 can detect, as the pupil dilation event data 31, the size or diameter of the user's pupil. In another arrangement, the controller 25 can detect, as the pupil dilation event data 31, pupil dilation variance data. For example, the controller 25 can calculate pupil dilation variance, or rate of change of a user's pupil dilation, by taking the temporal derivative of the user's pupil dilation at the time of collection of either the fixation event data 27 or saccade event data 29.

The cognitive load detection device 14 is configured as a computerized device, such as a personal computer, laptop, or tablet and can include a controller 35, such as a processor and a memory. During operation, as will be described in detail below, the cognitive load detection device 14 is configured to receive eye-movement data 26, which includes a combination of pupil dilation event data 31 and at least one of fixation event data 27 and saccade event data 29, from the eye-tracking device 12 and predict a user's cognitive load. For example, the cognitive load detection device 14 can include a classification function 70 which is configured to predict the user's cognitive load based upon the received eye-movement data 26.

In one arrangement, the cognitive load detection device 14 can be preconfigured with a classification function 70 developed by a third-party, such as a service provider 80. Prior to being provided to the cognitive load detection device 14, the third-party can train the classification function 70 with a training data set 82 which includes collected eye movement data (e.g., saccade event and or fixation event data) as well as corresponding task conditions (e.g., relatively high cognitive or relatively low cognitive loading) under which the eye movement data was collected. As a result of the training, the classification function 70 can receive the eye-movement data 26 without information about the associated task condition and predict the cognitive load associated with the eye-movement data 26.

In one arrangement, each of the eye-tracking device 12 and the cognitive load detection device 14 are configured as standalone devices disposed in electrical communication with each other. In one arrangement, the visual tracking system 10 includes both the eye-tracking device 12 and the cognitive load detection device 14 as part of a single device.

The controller 35 of the cognitive load detection device 14 can store an application for cognitive load detection. The cognitive load detection application installs on the controller 35 from a computer program product 30. In some arrangements, the computer program product 30 is available in a standard off-the-shelf form such as a shrink wrap package (e.g., CD-ROMs, diskettes, tapes, etc.). In other arrangements, the computer program product 30 is available in a different form, such downloadable online media. When performed on the controller 35 of the cognitive load detection device 14, the cognitive load detection application causes the cognitive load detection device 14 to predict the cognitive load of a user and to provide feedback to improve the user's visual interaction with the field of view.

Figure 2:
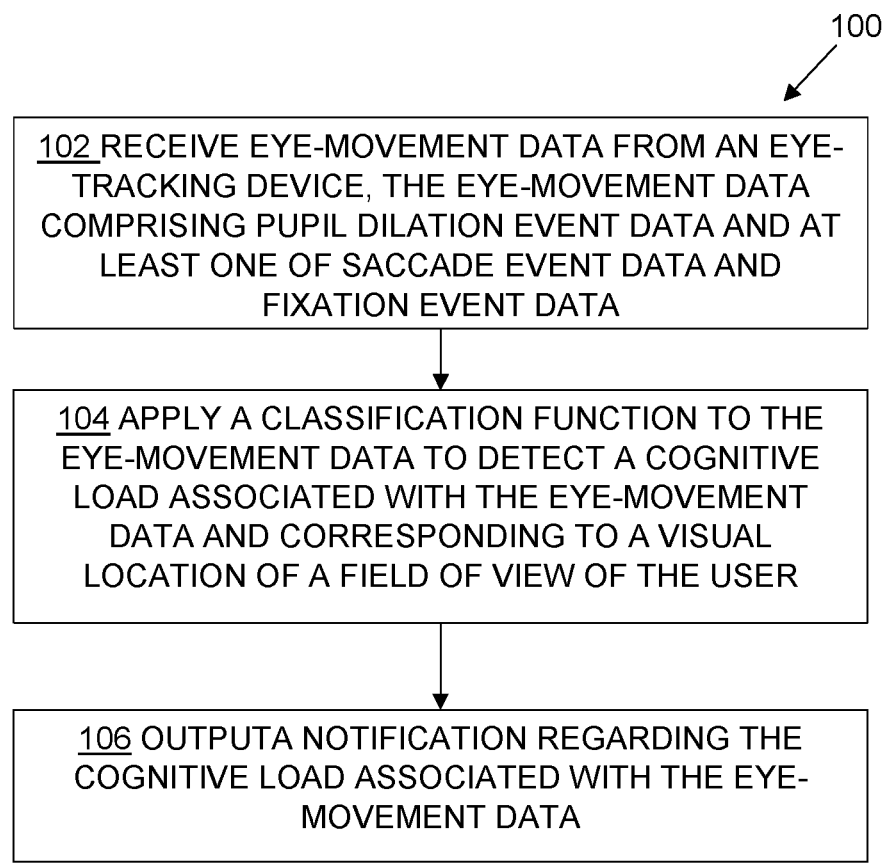
FIG. 2 illustrates a flow chart of a procedure performed by a cognitive load detection device of the visual tracking system of FIG. 1, according to one arrangement.

FIG. 2 illustrates a flow chart 100 of a procedure performed by the cognitive load detection device 14 of the visual tracking system 10 of FIG. 1 when detecting cognitive load.

In element 102, the cognitive load detection device 14 is configured to receive eye-movement data 26 from the eye-tracking device 12, the eye-movement data 26 comprising pupil dilation event data 31 and at least one of saccade event data 29 and fixation event data 27. For example, during operation and with reference to FIG. 1, the eye-tracking device 12 is configured to detect a user's eye movement as related to either a fixation event or a saccade event. Further, the eye-tracking device 12 is also configured to detect a pupil dilation event during the fixation or saccade event. For example, the eye-tracking device 12 can determine the diameter of the user's pupil or the rate of change of the user's pupil dilation as the pupil dilation event during either the fixation or saccade event. As a result, the eye-tracking device 12 can transmit eye-movement data 26-1 to the cognitive load detection device 14 that identifies the saccade event data 29 along with the corresponding pupil dilation event data 31 or eye-movement data 26-2 that identifies the fixation event data 27 along with the corresponding pupil dilation event data 31.

Returning to FIG. 2, in element 104, the cognitive load detection device 14 is configured to apply a classification function 70 to the eye-movement data 26 to detect a cognitive load 75 associated with the eye-movement data 26 and corresponding to a visual location 22 of a field of view of the user. As provided above, the classification function 70 can be developed to predict the cognitive load 75 associated with the eye-movement data 26 based on a training data set 82. In one embodiment, the classification function 70 can be configured to predict the user's cognitive load based upon a pupil dilation event associated with a saccade event. Alternately, the classification function 70 can be configured to predict the user's cognitive load 75 based upon a pupil dilation event associated with a fixation event. For example, based upon the application of the classification function 70 to the eye-movement data 26, the cognitive load detection device 14 can identify the user's cognitive load 75 as being relatively low or as being relatively high.

In element 106, the cognitive load detection device 14 is configured to output a notification 200 regarding the cognitive load 75 associated with the eye-movement data 26. In one arrangement, the cognitive load detection device 14 can generate the notification 200 to provide specific feedback relating to the cognitive load 75 depending upon the intended recipient of the notification 200.

In one arrangement, with reference to FIG. 1, the cognitive load detection device 14 can output a user notification 201 to the user, such as via the display 16, where the user notification 201 provides feedback regarding the user's detected cognitive load 75. For example, assume the case where the cognitive load detection device 14 identifies the user's cognitive load 75 as being relatively high. In such a case, the cognitive load detection device 14 can provide, as the user notification 201, suggestions for making the user's interaction with the display 16 easier in order to improve the user experience for the user. In another example, assume the case where the cognitive load detection device 14 identifies the user's cognitive load 75 as being relatively low, such as indicative of a user's lack of interest in one or more viewing locations 21 associated with the display 16. In such a case, the cognitive load detection device 14 can provide, as the user notification 201, a message or image to increase the user's interest in the viewing locations 21.

In one arrangement, with continued reference to FIG. 1, the cognitive load detection device 14 can output a service provider 202 notification to a service provider 80 where the service provider notification 202 identifying the eye-movement data 26 and the detected cognitive load 75. Such a notification 202 can be utilized by the service provider 80 for further development or refinement of the classification function 70. For example, assume the case where the service provider 80 is configured to provide updated classification functions 70 to the cognitive load detection device 14 over time. Because the service provider notification 202 identifies the eye-movement data 26 and the detected cognitive load 75, the service provider 80 can utilize the notification 202 to update the training data set 82. In turn, the service provider 80 can apply the updated training data set 82 to the classification function 70 to further refine its accuracy in predicting a user's cognitive load.

While the cognitive load detection device 14 can receive the eye-movement data 26 from the eye-tracking device 12 in a variety of ways, in one arrangement, the cognitive load detection device 14 is configured to receive the eye-movement data 26 as part of a substantially real-time stream. For example, cognitive load detection device 14 can continue to receive subsequent eye-movement data elements 26-N from the cognitive load detection device 14 as a substantially real-time stream. As the cognitive load detection device 14 receives the eye-movement data 26-N, the cognitive load detection device 14 can apply the classification function 70 to each eye-movement data element 26-N of the stream to provide real time analysis of the eye-movement data 26 during operation over a time period. This allows the cognitive load detection device 14 to identify and monitor the user's cognitive load relative to the display 16 on a substantially ongoing basis.

By utilizing combined fixation event and saccade event data with the pupil dilation event data, the cognitive load detection device 14 can predict a user's cognitive load with a relatively high degree of accuracy. Further, by detecting cognitive load through the analysis of eye-movement data 26, the cognitive load detection device 14 can respond to the user's needs via the notification 202 to assist in the adjustment of the user's cognitive load.

Figure 3:
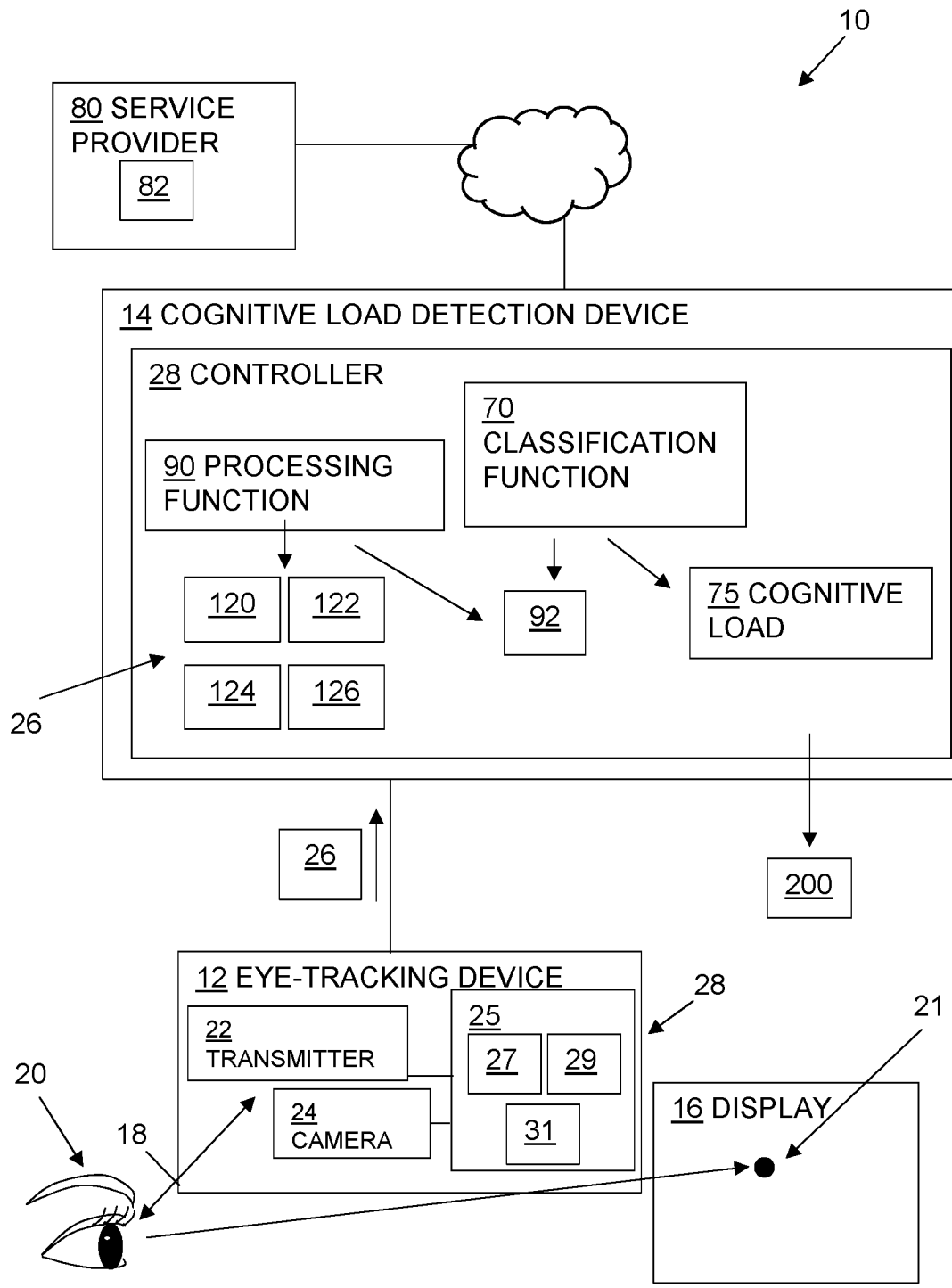
FIG. 3 illustrates a schematic diagram of a visual tracking system where a cognitive load detection device is configured to execute a processing function, according to one arrangement.

As provided above, the cognitive load detection device 14 is configured to apply the classification function 70 to the eye-movement data 26 which is a combination of either fixation event data 27 or saccade event data 29 with pupil dilation event data 31. In one arrangement, with reference to FIG. 3, the prior to the application of the classification function 70, the cognitive load detection device 14 is configured to apply a processing function 90 to the eye-movement data 26 to generate processed eye-movement data 92. The processing function 90 is configured to adjust the eye-movement data 92 to increase the performance or accuracy of the classification function 70 when predicting a user's cognitive load. Following generation of the processed eye-movement data 92, the cognitive load detection device 14 can apply the classification function 70 to the processed eye-movement data 92 to detect a cognitive load 75 associated with the processed eye-movement data 92 and can output a notification 200 relating to the cognitive load associated with the processed eye-movement data 92.

The processing function 90 can be configured in a variety of ways. In one arrangement, the processing function 90 can be configured to generate a ratio of a pupil dilation event data taken during a saccade event relative to a pupil dilation event data taken during a fixation event. For example, as provided above, the cognitive load detection device 14 can receive a stream of eye-movement data 26 from the eye-tracking device 12. In such a case, the stream of eye-movement data 26 can include eye-movement data elements 120 having pupil dilation event data taken during a saccade event and eye-movement data elements 122 having pupil dilation event data taken during a fixation event. As the cognitive load detection device 14 receives the eye-movement data elements 120, 122 over a period of time, application of the processing function 90 can average all of the eye-movement data elements 120 relating to the pupil dilation event data taken during saccade events and can average all of the eye-movement data elements 122 relating to the pupil dilation event data taken during fixation events. Further, application of the processing function 90 can create a ratio between these two averages (Pupil Dilation$_{SACCADE}$/Pupil Dilation$_{FIXATION}$) to generate the processed eye-movement data 92.

In one arrangement, the processing function 90 can be configured to generate a standard deviation of a ratio of the pupil dilation event data taken during the saccade event relative to the pupil dilation event data taken during the fixation event. For example, as provided above, the cognitive load detection device 14 can receive a stream of eye-movement data 26 which includes eye-movement data elements 120 having pupil dilation event data taken during a saccade event and eye-movement data elements 122 having pupil dilation event data taken during a fixation event. As the cognitive load detection device 14 receives the eye-movement data elements 124, 126 over a period of time, application of the processing function 90 can determine the standard deviation of each of the sets of eye-movement data elements 120, 122. Further, application of the processing function 90 can create a ratio between these two sets of standard deviations (Pupil Dilation$_{SACCADE}$/Pupil Dilation$_{FIXATION}$) to generate the processed eye-movement data 92.

In one arrangement, the processing function 90 can be configured to generate a generates a standard deviation of a ratio of the pupil dilation variance data taken during the saccade event relative to the pupil dilation variance data taken during the fixation event. As provided above, the cognitive load detection device 14 can receive a stream of eye-movement data 26 from the eye-tracking device 12 which can include eye-movement data elements 124 having pupil dilation variance data taken during a saccade event and eye-movement data elements 126 having pupil dilation variance data taken during a fixation event. As the cognitive load detection device 14 receives the eye-movement data elements 124, 126 over a period of time, application of the processing function 90 can determine the standard deviation of each of the sets of eye-movement data elements 124, 126. Further, application of the processing function 90 can create a ratio between these two sets of standard deviations (Pupil Dilation Variance$_{SACCADE}$/Pupil Dilation Variance$_{FIXATION}$) to generate the processed eye-movement data 92.

Figure 4:
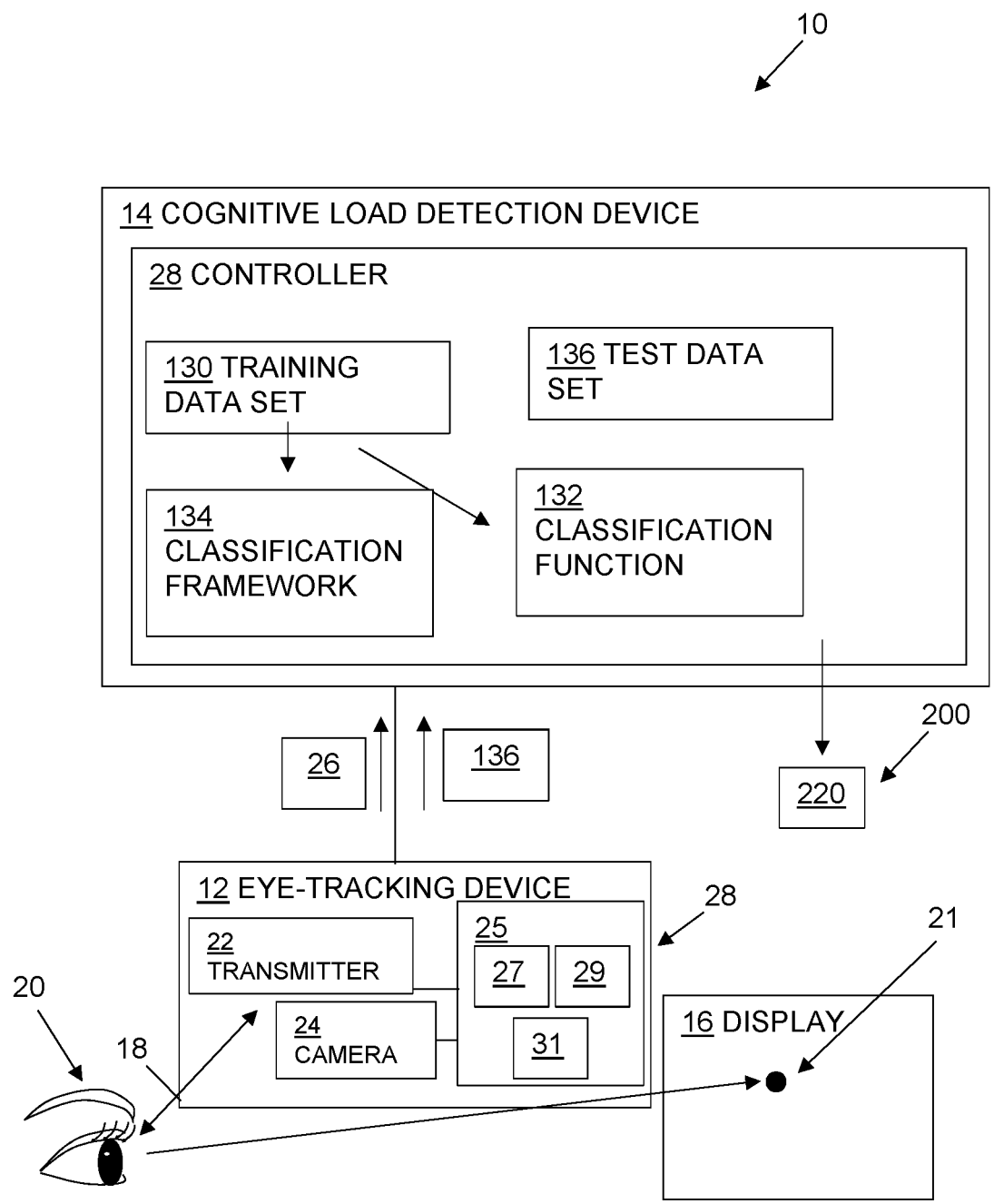
FIG. 4 illustrates a schematic diagram of a visual tracking system where a cognitive load detection device is configured to develop a training data set and classification function, according to one arrangement.

As indicated above, the cognitive load detection device 14 can be preconfigured with a classification function 70 developed by a third-party. Such indication is be way of example only. In one arrangement, as indicated in FIG. 4, the cognitive load detection device 14 is configured to build a training data set 130 that includes a set of eye movement inputs and corresponding set of task condition inputs and to generate a classification function 132 customized to the user of the visual tracking system 10.

In order to build the training data set 130, the cognitive load detection device 14 can provide the user with a number of tasks to be performed, such as tasks involving the display 16 (e.g., reading relatively easy/hard text passages, solving relatively easy/hard math problems, etc.). As the user performs the requested tasks, the cognitive load detection device 14 can retrieve the user's eye movement data 26 (saccade, fixation, pupil dilation) as the eye movement inputs. The cognitive load detection device 14 can also request the user to provide cognitive load feedback information 136 associated with the tasks as task condition inputs. For example, following the tasks, the cognitive load detection device 14 can request that the user rank the task condition (e.g., easy/hard) related to the task. For each task, the cognitive load detection device 14 can develop the training data set 130 to include, as the eye movement inputs, the eye movement data (e.g., saccade, fixation, pupil dilation) and, as the task condition inputs, the corresponding task condition rank (e.g., cognitive load) provided by the user.

Having developed the labeled training data set 130 based for a particular user, the cognitive load detection device 14 can train a classification framework 134 with the training data set to generate the classifier function 132. As indicated above, the classification function 132 is configured to identify whether the cognitive load detection device 14 captures a user's eye-movement data 26 during relatively lower or higher levels of task demand. However, the classification function 132 is based upon a particular framework 134. For example, the cognitive load detection device 14 can utilize a Random Forest (RF) framework to develop the classification function 132. Alternately, the cognitive load detection device 14 can utilize other frameworks, such as a deep learning framework or a neural network framework to develop the classification function 132.

In one arrangement, the cognitive load detection device 14 divides the development of the classification function 132 into two phases. In the first phase, the cognitive load detection device 14 trains the classification framework 134 with the paired set of eye movement data and task condition data provided by the training data set 130. During this training phase, the cognitive load detection device 14 can access both the collected eye movement data 26 as well as the task condition under which the data is collected, both of which are contained within the training set of data 130. Based upon the data available within the training data set 130, the cognitive load detection device 14 can train the classification framework 134, such as a Random Forest classification framework and fit the classification framework 134 to the data set 130 to generate the classification function 132.

In the second phase, the cognitive load detection device 14 tests the classification function 132 to assess the success of the training phase. In one arrangement, the cognitive load detection device 14 can use a test data set 136 to assess the performance of the trained classifier function 132. For example, the cognitive load detection device 14 can execute a performance assessment by measuring a level of error in answering questions about the task condition on the test data set 136. With a successful training, the cognitive load detection device 14 can receive subsequent eye-movement data 26 (i.e., without information about task condition) and reliably detect the task condition, or cognitive load, under which the eye movement data 26 was collected.

In one arrangement, in the case where the classifier function 132 has been developed and calibrated for a particular user, the cognitive load detection device 14 can be configured to provide the user with a customized or personalized notification 220 regarding the particular user's cognitive load 75 associated with the eye-movement data 26, such as suggestions to reduce the user's cognitive load. For example, assume a case where the user is involved in a decision making process among several items for sale and, as part of the process, views several pieces of information provided by the display 16. During this process, the cognitive load detection device 14 can receive eye-movement 26 data from the eye-tracking device 12 and can detect a relatively high cognitive load associated with viewing of these items. As a result, the cognitive load detection device 14 can provide a personalized notification 220 to the user to suggest that the user focus on the top 2 or 3 pieces of information that are relevant and important to the user (e.g., price, need, etc.). By providing the personalized notification 220, the cognitive load detection device 14 help to reduce the user's cognitive load by helping the user to make a decision based on a reduced, but most pertinent, amount of information.

As described above, cognitive load detection device 14 is configured to receive eye-movement data 26 which includes a combination of pupil dilation event data 31 and at least one of fixation event data 27 and saccade event data 29. Such description is by way of example only. In one arrangement, cognitive load detection device 14 is configured to receive eye-movement data 26 which includes blink event data associated with the user. Blinking relates to the involuntary act of shutting and opening one's eyelids. Accordingly, the blink event data included with the eye-movement data 26 can relate to blink number over a given time frame and/or to blink duration. The eye-tracking device 12 can include the blink event data as part of the eye-movement data 26 either on its own, in combination with the pupil dilation event data/fixation event data, or in combination with the pupil dilation event data/saccade event data.

As provided above, the cognitive load detection device 14 is configured to apply a processing function 90 to the eye-movement data 26 to generate processed eye-movement data 92. As described, the processing function 90 is configured to generate ratios of the pupil dilation event data or the pupil dilation variance data. Such description is by way of example only. In one embodiment, the processing function 90 can be configured to generate a variety of types of processed eye-movement data 92. For example, the processing function 90 can be configured to generate a standard deviation of the pupil dilation variance data taken during a fixation event, a standard deviation of saccade amplitude, a normalized saccade duration, a standard deviation of pupil dilation during fixation, a standard deviation of blink duration, a standard deviation of saccade duration, and an average blink duration.

While various embodiments of the innovation have been particularly shown and described, it will be understood by those skilled in the art that various changes in form and details may be made therein without departing from the spirit and scope of the innovation as defined by the appended claims.

What is claimed is:

1. A visual tracking system, comprising:
   an eye-tracking device; and
   a cognitive load detection device disposed in electrical communication with the eye-tracking device, the cognitive load detection device comprising a controller having a memory and a processor, the controller configured to:
   receive eye-movement data from the eye-tracking device, the eye-movement data comprising pupil dilation event data taken during a saccade event and pupil dilation event data taken during a fixation event,
   apply a processing function to the eye-movement data to generate processed eye-movement data as a ratio of the pupil dilation event data taken during the saccade event relative to the pupil dilation event data taken during the fixation event,
   apply a classification function to the processed eye-movement data to detect a cognitive load associated with the processed eye-movement data and corresponding to a visual location of a field of view of the user, the cognitive load indicating an amount of cognitive resources used by a user when processing information, and
   output a notification regarding the cognitive load associated with the processed eye-movement data.

2. The visual feature tracking system of claim 1, wherein when outputting the notification regarding the cognitive load, the controller is configured to output a user notification to the user, the user notification providing feedback regarding the detected cognitive load.

3. The visual feature tracking system of claim 1, wherein when outputting the notification regarding the cognitive load, the controller is configured to output a service provider notification to a service provider, the service provider notification identifying the eye-movement data and the detected cognitive load.

4. The visual feature tracking system of claim 1, wherein the controller is configured to:
   build a training data set comprising a set of eye movement inputs and corresponding set of task condition inputs; and
   train a classification framework with the training data set to generate the classifier function.

5. The visual tracking system of claim 1, wherein:
   when receiving the eye-movement data from the eye-tracking device, the controller is configured to receive a stream of eye-movement data in substantially real time from the eye-tracking device; and
   when applying the classification function to the eye-movement data, the controller is configured to apply the classification function to each data element of the stream of eye-movement data to detect the cognitive load over a time period.

6. In a cognitive load detection device, a method for detecting cognitive load, comprising:
   receiving eye-movement data from an eye-tracking device, the eye-movement data comprising pupil dilation event data taken during a saccade event and pupil dilation event data taken during a fixation event;
   applying a processing function to the eye-movement data to generate processed eye-movement data as a ratio of the pupil dilation event data taken during the saccade event relative to the pupil dilation event data taken during the fixation event;
   applying a classification function to the processed eye-movement data to detect a cognitive load associated with the processed eye-movement data and corresponding to a visual location of a field of view of the user, the cognitive load indicating an amount of cognitive resources used by a user when processing information; and outputting a notification regarding the cognitive load associated with the processed eye-movement data.

7. The method of claim 6, wherein outputting the notification regarding the cognitive load comprises outputting a user notification to the user, the user notification providing feedback regarding the detected the cognitive load.

8. The method of claim 6, wherein outputting the notification regarding the cognitive load comprises outputting a service provider notification to a service provider, the service provider notification identifying the eye-movement data and the detected cognitive load.

9. The method of claim 6, further comprising:
building a training data set comprising a set of eye movement inputs and corresponding set of task condition inputs; and
training a classification framework with the training data set to generate the classifier function.

10. The method of claim 6, wherein:
receiving the eye-movement data from the eye-tracking device comprises receiving a stream of eye-movement data in substantially real time from the eye-tracking device; and
applying the classification function to the eye-movement data comprises applying the classification function to each data element of the stream of eye-movement data to detect the cognitive load over a time period.

11. A computer program product having a non-transitory computer-readable medium including computer program logic encoded thereon that, when performed on a controller of a cognitive load detection device causes the cognitive load detection device to:
receive eye-movement data from an eye-tracking device, the eye-movement data comprising pupil dilation event data taken during a saccade event and pupil dilation event data taken during a fixation event;
applying a processing function to the eye-movement data to generate processed eye-movement data as a ratio of the pupil dilation event data taken during the saccade event relative to the pupil dilation event data taken during the fixation event;
apply a classification function to the processed eye-movement data to detect a cognitive load associated with the processed eye-movement data and corresponding to a visual location of a field of view of the user, the cognitive load indicating an amount of cognitive resources used by a user when processing information; and
output a notification regarding the cognitive load associated with the processed eye-movement data.

12. The visual tracking system of claim 1 wherein the pupil dilation event data comprises one of a diameter of a user's pupil and a rate of change of a user's pupil dilation.

13. A visual tracking system, comprising:
an eye-tracking device; and
a cognitive load detection device disposed in electrical communication with the eye-tracking device, the cognitive load detection device comprising a controller having a memory and a processor, the controller configured to:
receive eye-movement data from the eye-tracking device, the eye-movement data comprising pupil dilation event data taken during a saccade event and pupil dilation event data taken during a fixation event,
apply a processing function to the eye-movement data to generate processed eye-movement data as a ratio of a standard deviation of the pupil dilation event data taken during the saccade event relative to a standard deviation of the pupil dilation event data taken during the fixation event,
apply a classification function to the processed eye-movement data to detect a cognitive load associated with the processed eye-movement data and corresponding to a visual location of a field of view of the user, the cognitive load indicating an amount of cognitive resources used by a user when processing information, and
output a notification regarding the cognitive load associated with the processed eye-movement data.

14. A visual tracking system, comprising:
an eye-tracking device; and
a cognitive load detection device disposed in electrical communication with the eye-tracking device, the cognitive load detection device comprising a controller having a memory and a processor, the controller configured to:
receive eye-movement data from the eye-tracking device, the eye-movement data comprising pupil dilation variance data taken during a saccade event and pupil dilation variance data taken during a fixation event,
apply a processing function to the eye-movement data to generate processed eye-movement data as a ratio of a standard deviation of the pupil dilation variance data taken during the saccade event relative to a standard deviation of the pupil dilation variance data taken during the fixation event,
apply a classification function to the processed eye-movement data to detect a cognitive load associated with the processed eye-movement data and corresponding to a visual location of a field of view of the user, the cognitive load indicating an amount of cognitive resources used by a user when processing information, and
output a notification regarding the cognitive load associated with the processed eye-movement data.

15. In a cognitive load detection device, a method for detecting cognitive load, comprising:
receiving eye-movement data from an eye-tracking device, the eye-movement data comprising pupil dilation event data taken during a saccade event and pupil dilation event data taken during a fixation event;
applying a processing function to the eye-movement data to generate processed eye-movement data a ratio of a standard deviation of the pupil dilation event data taken during the saccade event relative to a standard deviation of the pupil dilation event data taken during the fixation event;
applying a classification function to the processed eye-movement data to detect a cognitive load associated with the processed eye-movement data and corresponding to a visual location of a field of view of the user, the cognitive load indicating an amount of cognitive resources used by a user when processing information; and
outputting a notification regarding the cognitive load associated with the processed eye-movement data.

16. In a cognitive load detection device, a method for detecting cognitive load, comprising:
receiving eye-movement data from an eye-tracking device, the eye-movement data comprising pupil dilation variance data taken during a saccade event and pupil dilation variance data taken during a fixation event;

applying a processing function to the eye-movement data to generate processed eye-movement data as a ratio of a standard deviation of the pupil dilation variance data taken during the saccade event relative to a standard deviation of the pupil dilation variance data taken during the fixation event;

applying a classification function to the processed eye-movement data to detect a cognitive load associated with the processed eye-movement data and corresponding to a visual location of a field of view of the user, the cognitive load indicating an amount of cognitive resources used by a user when processing information; and outputting a notification regarding the cognitive load associated with the processed eye-movement data.

* * * * *